(12) United States Patent  
Bae et al.

(10) Patent No.: US 8,847,007 B2
(45) Date of Patent: Sep. 30, 2014

(54) METHOD FOR PREPARING A GENETICALLY MODIFIED GRASS HAVING INFERTILENESS

(75) Inventors: Tae Woong Bae, Jeju-si (KR); Joon Ki Kim, Incheon (KR); In Ja Song, Jeju-si (KR); Pyung Ok Lim, Jeju-si (KR); Pill Soon Song, Jeju-si (KR); Hyo Yeon Lee, Jeju-si (KR); Si Yong Kang, Jeonbuk (KR); Hong-Gyu Kang, Daegu (KR); Yong-Pyo Lim, Daejeon (KR)

(73) Assignees: Cheju National University Industry—Academic Cooperation Foundation, Jeju-si (KR); The Industry & Academic Cooperation in Chungnam National University, Daejeon (KR)

( * ) Notice: Subject to any disclaimer, the term of this patent is extended or adjusted under 35 U.S.C. 154(b) by 506 days.

(21) Appl. No.: 13/000,011

(22) PCT Filed: Jun. 17, 2009

(86) PCT No.: PCT/KR2009/003246
§ 371 (c)(1),
(2), (4) Date: Dec. 17, 2010

(87) PCT Pub. No.: WO2009/154400
PCT Pub. Date: Dec. 23, 2009

(65) Prior Publication Data
US 2011/0107454 A1    May 5, 2011

(30) Foreign Application Priority Data
Jun. 17, 2008  (KR) .............................. 2008-0056663

(51) Int. Cl.
*A01H 1/02* (2006.01)
*A01H 1/04* (2006.01)

(52) U.S. Cl.
USPC ............ 800/276; 800/270; 800/300; 800/320

(58) Field of Classification Search
None
See application file for complete search history.

(56) References Cited

U.S. PATENT DOCUMENTS

2007/0044173 A1*  2/2007  Wang et al. ................... 800/278

OTHER PUBLICATIONS

H.-W. Fu et al. (Mol Breeding (2008) 22:281-288).*
Reichman et al. (Molecular Ecology (2006) 15, 4243-4255).*
Beck et al. (Seed Sci. & Technol., (2007) 35, 351-359).*
International Search Report, mailing date Jan. 12, 2010, for corresponding International Application No. PCT/KR2009/003246 with English translation.

* cited by examiner

*Primary Examiner* — David T Fox
*Assistant Examiner* — Jared Shapiro
(74) *Attorney, Agent, or Firm* — Intellectual Property Law Group LLP

(57) ABSTRACT

A method is provided for preparing infertility-induced, genetically modified grass. It comprises a) exposing a flower of genetically modified grass to a physical mutagen; (b) culturing the genetically modified grass exposed to the physical mutagen to produce seeds thereof; and (c) culturing the seeds to select an infertility-induced species.

6 Claims, 3 Drawing Sheets

(A)

(B)

(A)

(B)

METHOD FOR PREPARING A GENETICALLY MODIFIED GRASS HAVING INFERTILENESS

TECHNICAL FIELD

The present invention relates to a method for the preparation of infertility-induced, genetically modified grass.

BACKGROUND ART

The rapid paces of global warming soil impoverishment and industrialization are greatly decreasing the area of farm land across the globe. Also, the ban on the use of chemical fertilizers for environmental preservation reasons is decreasing worldwide crop production while the population of the world is exceeding the production rate of crops.

Therefore, solving such food problems is a challenge being faced by the mankind. Genetically modified organisms (GMO), prompted by bioengineering techniques, are becoming solution to the food problems.

A genetically modified organism is an organism whose genetic material has been altered using genetic engineering techniques, such as recombinant DNA technology, for example, to increase crops.

Since the development of ripening-delayed, genetically modified tomatoes by Calgene in 1994, the commercialization of genetically modified crops started with the pesticide-resistant soybeans of Monsanto and the insect-resistant corn of Novatis and has progressed to insect-resistant rice (Tu et al., 2000), vitamin A-enriched rice (Ye et al., 2000) and iron-enriched rice (Vasconcelos et al., 2003).

As many as 100 species have been genetically modified (Mohan Babu et al., 2003), including soybeans, corns, wheat, tomatoes, potatoes, and rice. Their cultivation reportedly amounted to 1.7 millions ha in 1996 and increased to 67.7 millions ha in 2003 (James, 2004).

Although developed to give humans beneficial effects including resistance to pesticides, diseases and insects, genetically modified crops are being controversial about hazards to humans and environments due to the flow of modified genes.

The gene flow of genetically modified crops is typically achieved by the migration of genetically modified crops themselves and their seeds and by pollen transportation.

Thus far, pollen transportation has made the strongest contribution to gene flow. Being likely to modify the genetic traits of homologous and allied species, the pollen-mediated gene flow has the risk of disturbing the environmental ecosystem (Karevar et al., 1994).

Pollen-mediated gene flow from herbicide-resistant oilseed rape (*Brassica napus*) was found in an area 3 km away from the donor field (Rieger et al., 2002), As for herbicide-resistant creeping bantgrass, the distance over which it was dispersed was extended up to 21 km (Watrud et al., 2004).

Given this background, the present invention was conceived to prevent the pollen-mediated gene of genetically modified grass.

DISCLOSURE

Technical Problem

It is an object of the present invention to provide a method for the preparation of infertility-induced, genetically modified grass.

Other features and concrete embodiments of the present invention will be given below.

Technical Solution

The present invention discloses a technique of blocking the pollen-mediated gene flow of genetically modified grass.

As will be described later, Basta herbicide-resistant grass (*Zoysia japonica*) was used as a genetically modified organism. It was exposed to gamma radiation at flowering time and its seeds were gathered, germinated and allowed to grow into adult plants. Observations showed that 4% of the plants (9 of 223) were induced with infertility.

Based on these experimental data, the present invention is provided.

In accordance with an aspect thereof, the present invention provides a method for preparing infertility-induced, genetically modified grass, comprising (a) exposing a flower of genetically modified grass to a physical mutagen, (b) culturing the genetically modified grass exposed to the physical mutagen to produce seeds thereof, and (c) culturing the seeds to select an infertility-induced species.

As used herein, the term "grass" is intended to refer to all species of grass. Examples of the grass include those belonging to *Paspalum* sp., *Agrostis* sp., *Cynodon* sp., *Festuca* sp., *Poa* sp., *Lolium* sp., *Stenotaphrum* sp., and *Zoysia* spp., with preference for Bahia Grass, *Paspalum notatum*, Bentgrass (*Agrostis stolonifera, Agrostis capillaries*), Bermuda Grass (*Cynodon dactylon*), Fescue (*Festuca arundinacea*), Kentucky Blue Glass (*Poa pratensis*), Rye Grass (*Lolium perenne*), St. Augustine Grass (*Stenotaphrum secundatum*), *Zoysia japonica, Zoysia matella, Zoysia tenuifolia, Zoysia macrotachya* and *Zoysia sinica*.

As used herein, the term "genetically modified grass" is intended to refer to grass in which a desired genetic trait is artificially introduced by a genetic manipulation technique such as genetic recombination, treatment with a chemical or physical mutagen, so on. Examples of the artificially introduced genetic traits include herbicide resistance, dwarfism, and insect and disease resistance, with pa reference for herbicide resistance and a greater preference for Basta herbicide resistance.

The term "flower of grass" means a reproductive structure of a grass in which the flowering organs including pistils, stamens, petals and receptacles are well developed. Typically, blossoming starts with the formation of a flower bud, followed by the growth of floral axis from which flower organs such as pistils, stamens, petals and receptacles differentiate and develop. Therefore, a "flower of grass" is intended to refer to a flower at any time over the entire lifespan of a flower from the differentiation of flower organs after the formation of flower buds to the death of the flower.

The reason for exposing a flower of grass to a mutagen is because a high yield of mutagenesis may be achieved at flowering time which is when pollination and fertilization occur. For reference, when the seeds of grass are treated with mutagens, particularly with chemical mutagens (EMS, EES (ethyl ethane sulfonate), EO (Ethylene oxide), NMC, so on), no infertility was induced in the grass.

As used herein, the term "infertility" is intended to refer to the inability of a grass to sexually reproduce. It may be understood as a non-bolting, genetic trait (e.g., unable to produce flower buds and stalks) or a trait resulting from the non-bolting (e.g., unable to produce seeds).

As used herein, the term "infertility-induced" is intended to refer to the genetic mutation by which the mutant character, that is, infertility is expressed in the next generation. Grasses including *Zoysia* spp. have the capability of vegetative reproduction via subterranean stems and stolons. Thus, the sentence "infertility is expressed in the next generation" may be understood to mean that even when grasses vegetatively reproduce through subterranean stems and stolons, the new individuals still remain infertile.

Examples of the physical mutagen useful in the present invention include X rays, γ radiation ($^{60}$Co), β radiation ($^{32}$P, $^{35}$S, etc) and a neutron beam (Hasegawa et al. 1995; Ling et al. 1991; Wang et al. 1988; Honda et al. 2006; Naito et al. 2005), with preference for γ radiation from $^{60}$Co.

The period of time for which grasses are irradiated with the physical mutagen may be determined by those skilled in the art in consideration of the kind of the mutagen employed. Typically, the time period of exposure to a physical mutagen with a stronger radiation intensity may become shorter to perform desired mutagenesis.

So long as it can used to introduce infertility into grasses, the present invention imposes no limitations on the physical mutagen that may be used, time period of treatment, etc.

However, it is understood from the following Example section that irrespective of its kind, the physical mutagen is irradiated preferably at a dose of from 10 to 100 Gy, more preferably at a dose of from 10 to 50 Gy. A preferred source of the physical mutagen is $^{60}$Co.

In the present invention, preferably, the infertility-induced grass is also genetically induced to show dwarfism.

The term "dwarfism" is intended to refer to the genetic trait of a grass of interest being smaller in size (or biomass) than the wild-type. In detail, the grass is shorter in height, the internodes are closer, and the length and/or width are less than the wild-type.

As used herein, the term "genetically induced to show dwarfism" is intended to mean that the grass undergoes such a genetic mutation that the mutant character of dwarfism is expressed in the next generation. Thus, the sentence "the mutant character of dwarfism is expressed in the next generation" may be understood to mean that even when grasses vegetatively reproduce through subterranean stems and stolons, the new individuals still remain dwarf.

The dwarfism character of grasses is closely related to labor-saving in mowing grasses.

The infertility-induced, genetically modified grass can be selected on the basis of the formation of flower buds and stalks. In addition, the number of leaf-node stages may be used as a standard for determining the induction of infertility in the grass.

In accordance with another aspect thereof, the present invention pertains to a method for preparing subterranean stems of infertility-induced, genetically modified grass.

The method for preparing subterranean stems of infertility-induced, genetically modified grass comprises (a) treating a flower of genetically modified grass with a physical mutagen, (b) culturing the mutagen-treated, genetically modified grass to produce seeds thereof, (c) culturing the seeds to select an infertility-induced species, and (d) gathering subterranean stems from the fertility-induced, genetically modified grass.

In a further aspect thereof the present invention pertains to a method for preparing stolons of infertility-induced, genetically modified grass.

The method for preparing subterranean stems of infertility-induced, genetically modified grass comprises (a) treating a flower of genetically modified grass with a physical mutagen, (b) culturing the mutagen-treated, genetically modified grass to produce seeds thereof, (c) culturing the seeds to select an infertility-induced species, and (d) gathering stolons from the fertility-induced, genetically modified grass.

The subterranean stems or stolons prepared according to the methods of the present invention are useful for propagating the infertility-induced, genetically modified grass.

In the methods, preferably, the infertility-induced grass is also genetically induced to exhibit dwarfism.

In association with the preparation method of the subterranean stems or the stolons, the terms "grass", "genetically modified grass", "infertility" and "dwarfism" are as defined above.

In still a further aspect thereof, the present invention pertains to a method for propagating infertility-induced, genetically modified grass, comprising implanting the subterranean stems or stolons into soil and culturing them.

When the subterranean stems or the stolons are implanted thereinto, the soil may be bare ground (open soil) or may be soil contained within a pot.

Typical conditions for the cultivation of grasses may be applied for the propagation step of the method. As a matter of course, the conditions, such as light and temperature, may be changed to improve on the propagation yield.

Advantageous Effects

As described hitherto, a method is provided for preparing infertility-induced, genetically modified grass in accordance with the present invention. Fundamentally, the infertility-induced, genetically modified grass is prohibited from causing pollen-mediated gene flow, which is the major cause of the disturbances to and destruction of the ecosystem.

MODE FOR INVENTION

A better understanding of the present invention may be obtained through the following examples which are set forth to illustrate, but are not to be construed as limiting the present invention.

EXAMPLES

Preparation of Infertility-Induced, Genetically Modified Grasses

Example 1

Preliminary Experiments for Irradiation with Gamma Radiation ($^{60}$Co)

Example 1-1

Irradiation of Gamma Ray ($^{60}$Co) and Production of Seeds (M1)

The genetically modified grass used in this experiment was a T6 generation plant (Bae T W, Vanjildorj E, Song S Y, Nishiguchi S, Yang S S, Song I J, Chandrasekhar T, Kang T W, Kim J I, Koh Y J, Park S Y, Lee J, Lee Y E, Ryu K H, Riu K Z, Song P S, Lee H Y (2008) Environmental risk assessment of genetically engineered herbicide-tolerant Zoysia japonica. J. Environ. Qual. 37: 207-218) of the genetically modified grass with a Basta herbicide-resistant bar gene transformed thereinto (Zoysia japonica Steud.) (Toyama K, Bae C H, Kang J G, Lim Y P, Adachi T, Riu K Z, Song P S, Lee H Y (2003) Production of herbicide-tolerant zoysiagrass by Agrobacterium-mediated transformation Mol Cells. 16: 19-27), which was verified for the genetic stability of the foreign gene. The grass was implanted in a pot 25 cm long in diameter, and cultivated in a GMO greenhouse under sunshine without artificial lighting.

To determine optimal radiation doses, the genetically modified grass in its blossoming stage (suitable for pollination and fertilization, anthers grown ⅔ or greater of the full length thereof within the ears) was exposed to gamma radiation ($^{60}$Co).

Irradiation with gamma rays ($^{60}$Co) was performed at a rad dose of zero (non-treated), 10 Gy, 20 Gy, 30 Gy, 40 Gy, 50 Gy, 75 Gy and 100 Gy with the aid of an irradiation facility in the Applied Radiological Science Research Institute of Jeju National University.

After treatment with gamma radiation, the individual plants were cultured at 32° C.±7 in a greenhouse of Jeju National University under sunshine. After cultivation for 3 months, seeds (M1) were collected from each plant.

The seeds were dried for 3 days under sunshine and stored at −15° C. until used in a germination experiment.

Experiment 1-2

Germination Rate of Seeds M1

To increase the germination rate thereof, the M1 seeds after exposure to gamma radiation were immersed for 30 min in 5 M potassium hydroxide (Junsei, Japan) and then neutralized for 5 min with 1 M acetic acid (Junsei, Japan) to soften testas.

Next, the seeds were immersed for 15 min in 2% sodium hypochlorite (Daejung, Korea), washed five times with sterile water, and sowed on moisturized filter papers. The seeds were allowed to absorb water for 2 days under a dark condition, followed by cultivation at 32° C.±2 for 3 days under a continuous light condition (4,000 Lux) to induce germination.

Figure 1:
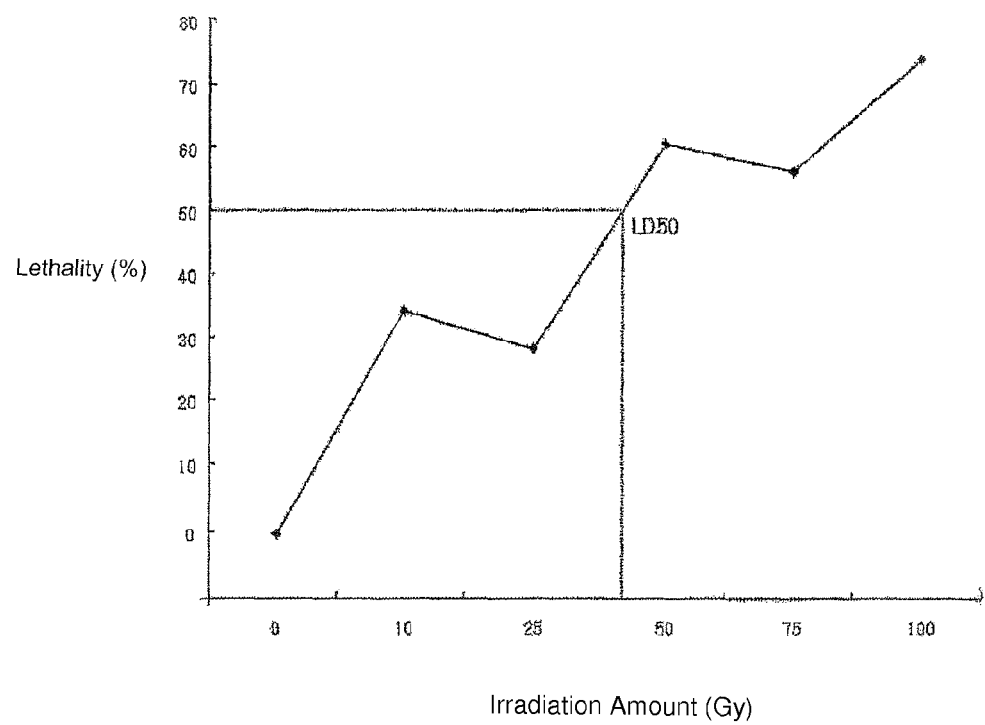
FIG. 1 is a graph in which the lethality of the springs of a genetically modified grass into which a bar gene responsible for resistance to Basta herbicide is introduced is plotted against radiation doses when seeds are allowed to germinate after they are produced from the genetically modified grass irradiated with gamma radiation from ($^{60}$Co) at a dose of 0 (non-treated), 10 Gy, 20 Gy, 30 Gy, 40 Gy, 50 Gy, 75 Gy and 100 Gy.

The mortality of seeds (percentage of non-germinated to total seeds) according to radio-treatment is depicted in FIG. 1. As seen in the plot of FIG. 1, the seeds withered at a rate of 32% on average with a dose of 10 to 25 Gy, at a rate of 59.5% with a dose of 50 to 75 Gy, and a rate of 75% with a dose of 100 Gy.

Taking account of these data, the seeds were determined to be exposed to a radiation dose of up to the LD50 value, that is, zero (non-treated), 10, 20, 30, 40 and 50 Gy.

Example 2

Induction of Infertility in Genetically Modified Grass by Irradiation with Gamma Radiation ($^{60}$Co), and Production and Germination of Seeds Thereof The genetically modified grasses were exposed to gamma radiation ($^{60}$Co) at a dose of 0, 10, 20, 30, 40 and 50 Gy and the M1 seeds were produced and germinated in the same manner as in Example 1.

Germination and survival rates are given in Table 1, below. The germination rates were calculated using the total number of the plants which had germinated for 5 weeks from the time of the initial germination. For the survival rates, the young plants germinated from the seeds were transplanted to pots, cultured for 8 months, and counted for living individuals.

TABLE 1

Germination and Survival Rates of Gamma Radiation-Treated Genetically Modified Zoysia Grass (M1)

| Dose (Gy) | No. of Seeds | No. of Germinated Seeds (Germination Rate %) | No. of Surviving plants (survival rate %) |
|---|---|---|---|
| Non-treated | 100 | 74 (74) | 70 (94) |
| 10 | 150 | 84 (56) | 42 (50) |
| 20 | 150 | 61 (41) | 42 (68) |
| 30 | 200 | 94 (47) | 56 (59) |
| 40 | 300 | 93 (31) | 64 (68) |
| 50 | 300 | 66 (22) | 19 (28) |

The surviving M1 plants (70 non-treated individuals and 223 treated individuals) were acclimated at 25° C.±7 for 3 months under sunshine in pots 10 cm in diameter and then transplanted to pots 15 cm in diameter. After cultivation therein at 25° C.±7 for 2 years, the plants were primarily examined for infertility. After transplantation into pots 25 cm in diameter, the plants were cultured at 25° C.±7 for 2 years under sunshine in a GMO greenhouse and then secondarily examined for infertility. In this regard, primary selection was made by determining whether the Zoysia grass showed bolting or unbolting characters. Then, the numbers of leaf-node stages of the selected individual plants were compared to further select infertile grasses.

Numbers of the bolted and unbolted plants are given in Table 2, below.

TABLE 2

Numbers of UnBolted/Bolted Plants and Their Percentage

| Dose (Gy) | No. of Survived Plants | No. of 2-yr. Unbolted Plants | No. of 4-yr Unbolted Plants |
|---|---|---|---|
| Non-Treated | 70 | 4 | 0 |
| 10 | 42 | 15 | 1 |
| 20 | 42 | 20 | 1 |
| 30 | 56 | 34 | 2 |
| 40 | 64 | 38 | 3 |
| 50 | 19 | 9 | 2 |

When cultured for 2 years, as shown in Table 2, the non-treated plants were unbolted at a rate of 5.7% (4/70) while the treated plants were unbolted at a rate of 52% ((15+20+34+38+9)/(42+42+56+64+19)). As for 4-year-plants, all of the non-treated plant were bolted while the treated plants were unbolted at a rate of 4% ((1+1+2+3+2)/(42+42+56+64+19)).

Grass of Zoysia spp. withers its leaves in the winter. When entering a growing period, the grass generates new leaves from a leaf-node stage next to a pre-existing one. Typically, when the leaf-node stages amount to 12, the grass undergoes bolting and blooms (Yeam D Y, Murray J J, Portz H L, Joo Y K (1985) Optimum seed coat scarification and light treatment for the germination of Zoysia grass (Zoysia japonica Steud) seed. J. Kor. Soc. Hort. Sci. 26: 179-185). Hence, the number of leaf-node stages can be used as an index for the blossom of grass of Zoysia spp.

For this reason, the numbers of leaf-node stages was counted. For two-year plants, the leaf-node stages were found to amount to 11.4 on average for unbolted plants and 13.6 on average for bolted plants. Hence, two-year unbolted plants were expected to be bolted later.

Returning to 4-year plants, the number of leaf-node stages of the bolted plants amounted to 14.8 on average when being untreated but to 15.7 on average when being treated. On the other hand, the unbolted plants were observed to have 15.4 leaf-node stages on average.

Figure 2:
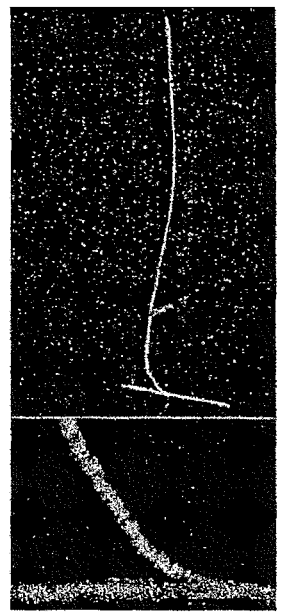
FIG. 2 is of photographs showing a comparison of the number of leaf-node stages between a non-treated, bolted plant (A) and a radiation-treated, non-bolted plant (B).
Figure 2:

With reference to FIG. 2, one bolted plant which was not treated with gamma radiation (A) and one unbolted plant which was treated with gamma radiation (B) are compared with regard to the number of leaf-node stages. In the photographs, the bar scales 1 cm.

In light of the knowledge of the cited articles, the unbolting of the radio-treated plants, even though having 15.4 leaf-node stages on average, indicates that infertility was induced therein.

Figure 3:
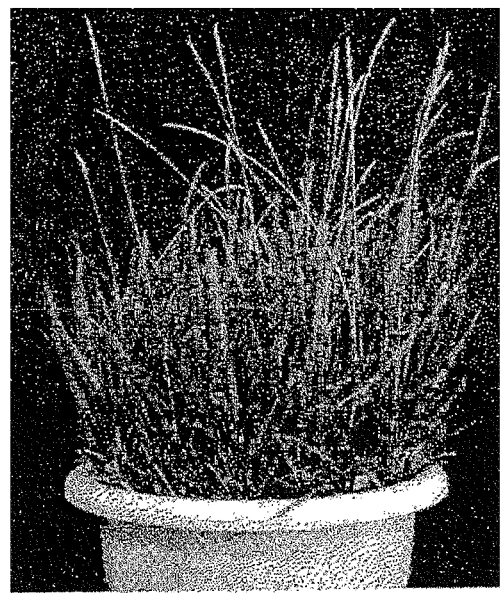
FIG. 3 is of photographs showing infertility-induced, genetically modified grasses with a dwarf phenotype and wild-type grasses.
Figure 3:
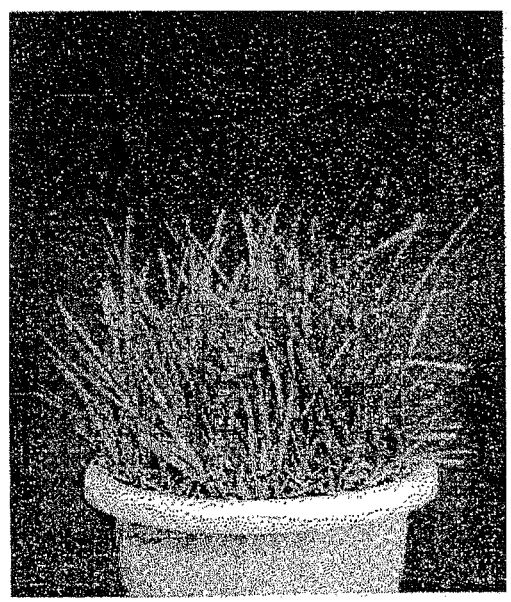

Of the 4-year unbolted plants, two exhibited a dwarf character one of which is shown, together with the wild-type, in FIG. 3.

We claim:

1. A method for preparing infertility-induced, genetically modified *Zoysia japonica*, comprising:
    (a) irradiating a flower of genetically modified *Zoysia japonica* with $^{60}$Co radiation at a rad dose of from 10 to 50 Gy;
    (b) culturing the $^{60}$Co-irradiated, genetically modified *Zoysia japonica* to produce seeds thereof; and
    (c) culturing the seeds to obtain infertility-induced plants by selecting unbolted plants;
    wherein the infertility-induced, genetically modified *Zoysia japonica* exhibits a genetic trait of unbolting.

2. The method according to claim 1, wherein the genetically modified *Zoysia japonica* exhibits herbicide resistance.

3. The method according to claim 1, wherein the *Zoysia japonica* exhibits a genetic trait of dwarfism.

4. A method for preparing subterranean stems or stolons of infertility-induced, genetically modified *Zoysia japonica*, comprising:
    (a) irradiating a flower of genetically modified *Zoysia japonica* with $^{60}$Co radiation at a rad dose of from 10 to 50 Gy;
    (b) culturing the $^{60}$Co-irradiated, genetically modified *Zoysia japonica* to produce seeds thereof;
    (c) culturing the seeds to obtain infertility-induced plants by selecting unbolted plants; and
    (d) gathering subterranean stems from the fertility-induced, genetically modified *Zoysia japonica;*
    wherein the infertility-induced, genetically modified *Zoysia japonica* exhibits a genetic trait of unbolting.

5. The method according to claim 4, wherein the genetically modified *Zoysia japonica* exhibits herbicide resistance.

6. The method according to claim 1, wherein the *Zoysia japonica* exhibits a genetic trait of dwarfism.

* * * * *